United States Patent [19]
Nordquist

[11] Patent Number: 5,127,829
[45] Date of Patent: Jul. 7, 1992

[54] MOLD FOR TAKING DENTAL IMPRESSIONS

[76] Inventor: Martin Nordquist, Södra Vägen 4, Harnosand, Sweden, 87140

[21] Appl. No.: 615,366

[22] Filed: Nov. 19, 1990

[51] Int. Cl.⁵ .............................................. A61C 9/00
[52] U.S. Cl. ..................................... 433/35; 433/37
[58] Field of Search ................ 433/37, 34, 35, 38

[56] References Cited

U.S. PATENT DOCUMENTS

| | | | |
|---|---|---|---|
| 755,670 | 3/1904 | Joannidi | 433/35 |
| 1,346,998 | 7/1920 | Veale | 433/35 |
| 2,312,171 | 2/1943 | Jochum | 433/35 |
| 3,576,075 | 4/1971 | Scott | 433/34 |
| 4,375,965 | 3/1983 | Weissman | 433/37 |
| 4,746,469 | 5/1988 | Yamashita | 433/37 |

FOREIGN PATENT DOCUMENTS 0800874  1/1951  Fed. Rep. of Germany ........ 433/34
461764   3/1990  Sweden .

*Primary Examiner*—Gene Mancene
*Assistant Examiner*—Adriene B. Lepiane
*Attorney, Agent, or Firm*—Hill, Van Santen, Steadman & Simpson

[57] ABSTRACT

A mold for taking impressions of the teeth including a substantially U-shaped bottom plate having a bottom surface which is bordered by an inner defining wall and an outer defining wall and a cover member including a perforated bottom. The cover member preferably is received within the bottom plate and separated from a bottom thereof by a spacer including an upwardly opening channel that registers with the perforations. Formed between the bottom part of the cover member and the bottom surface of the bottom plate are channels which function to conduct coolant through the mold. The mold is preferably made from a plastic material.

6 Claims, 4 Drawing Sheets

MOLD FOR TAKING DENTAL IMPRESSIONS

BACKGROUND OF THE INVENTION

The present invention relates to a mold for taking impressions of the teeth, said mold comprising a substantially U-shaped impression tray having a bottom surface which is surrounded by inner and outer defining walls. More specifically, the invention relates to double-bottomed trays adapted for flowing coolant within the double bottom.

Molds of the type to which the invention relates have been known for a long time and are manufactured both of metal and plastic materials. Metal molds can be configured either for use in an impression casting material that does not require forced cooling, or with a double bottom that enables a coolant to be conducted through the bottom of the mold so as to cool an impression casting material that requires forced cooling. Such double-bottom metal molds are normally manufactured in two parts that are subsequently soldered together. Plastic molds for taking dental impressions are used exclusively to take impressions with the aid of an impression casting material that does not require forced cooling.

In my prior Swedish Pat. No. 461764, issued Mar. 26, 1990, the teachings of which are fully incorporated herein, there is discussed a plastic mold for taking impressions of teeth which can be used both with impression casting material that does not require forced cooling and impression casting material that required forced cooling. The impression tray is provided with a snap-in cover member so that a double bottom is formed within which a coolant can be conducted.

SUMMARY OF THE INVENTION

The present invention is an improved mold for taking impressions of teeth which can be produced from a plastic material while still enabling the mold to be used with impressions casting material that does not require forced cooling and also impression cast material that requires forced cooling.

Additionally, the invention provides a dental impression tray with improved gripping of impression material therein. Yet further, the invention provides a mold adapted for improved formations of gypsum bases.

To these ends, an embodiment of the invention provides a dental impression tray including a cooperating snap-in cover member that engages within a U-shaped bottom plate in spaced apart fashion, the cover member including perforations along a bottom wall thereof so that impression material placed in the cover member will flow through the perforations and harden to provide a good grip for the impression material in the tray.

The cover member can be secured within the bottom plate by a suitable snap-in engagement construction. Alternatively, the cover member can be ultra-sonically welded to the bottom plate.

In a preferred embodiment, an elongated spacer or separator is positioned in the bottom plate of the impression tray along a bottom surface thereof and between the bottom surface and an underside of the cover member, the separator including an upwardly opening channel in registry with the perforations in the cover member so that the impression material seeps only into the channel.

In a particularly preferred embodiment, the channel opens on a bottom side of the bottom so that impression material can seep through the channel.

In another embodiment, the invention provides a base former that fits over an impression tray for use in making a gypsum base for an upper jaw impression, the base former including cut off corners at positions adjacent the back teeth so that the resulting gypsum base formed therewith includes cut off corners.

These and other features and aspects of the invention will become clearer below with reference to the following detailed description of the presently preferred embodiments and accompanying drawings.

DETAILED DESCRIPTION OF THE PRESENTLY PREFERRED EMBODIMENTS

Figure 1:
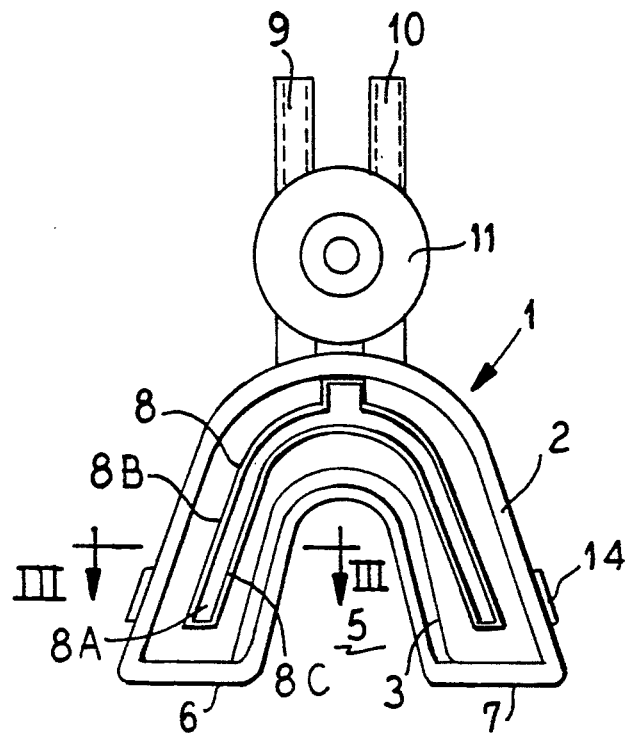
FIG. 1 is a plan view of a bottom plate of a mold for taking dental impressions in accordance with the invention.

In FIG. 1 there is illustrated a bottom plate 1 intended for use as a mold for taking impressions of the teeth. The bottom plate 1 has a substantially U-shaped configuration and has an outer defining wall 2 and an inner defining wall 3 that are mutually joined by a bottom surface 4. The mold illustrated in FIG. 1 is used to take a dental impression of the teeth in a patient's lower jaw and accordingly includes a palate-hole 5. The bottom plate 4 is terminated at the legs of the U by two ends 6 and 7.

Attached to the inside bottom surface 4 of the plate 1 is a separator or spacer 8, which starts from the crown of the plate and extends substantially centrally in both directions along the bottom surface 4 and terminates short of the ends 6 and 7. This separator or spacer 8 projects above the bottom surface and is intended to form a support for a cover member or mold insert 15 described hereinafter with reference to FIG. 4.

The separator 8 is constructed so that it includes a recess or channel 8A bounded by two upstanding walls 8B and 8C. The channel 8A preferably opens upwardly and downwardly. This can be seen most clearly in FIGS. 3 and 7.

Mounted on the crown of the bottom plate 1 are two ducts 9 and 10 that connect with the interior of the bottom plate 1 through openings appropriately formed in the outer defining wall 2 on both sides of the separator 8. These connecting ducts 9 and 10 are used to introduce coolant into and remove coolant from the bottom plate 1, as described in more detail below.

Mounted externally of the outer defining wall 2 and adjacent the crown of the plate 1 is a thumb grip 11 which extends over the two connecting ducts 9 and 10 and which is configured in a manner to facilitate removal of the mold from the mouth subsequent to hardening of the impression casting material in the mold. As is well-known, impression material will tightly embrace the teeth of the patient on which the mold is used, and consequently considerable force is required to remove the mold subsequent to hardening of the casting material.

Figure 2:
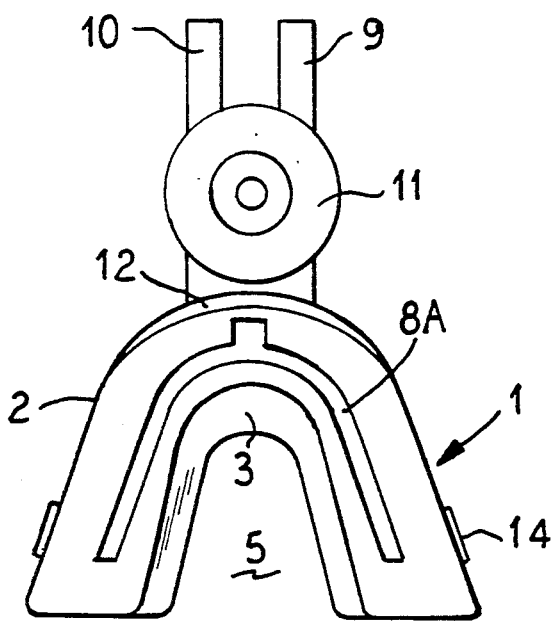
FIG. 2 is a view from beneath of the bottom plate illustrated in FIG. 1.

FIG. 2 is a view of the bottom plate 1 from beneath and illustrates that the bottom surface is substantially flat and that provided on the underside of the front edge of the bottom plate is a downwardly projecting camming surface 12 which is configured to form a suitable grip for the dentist taking the impression, such that the dentist can place his index finger against the rear side of the camming surface 12 and the grasp the thumb grip 11 with his thumb, so as to obtain a good grip on the mold when removing the mold when an impression has been taken.

Figure 3:
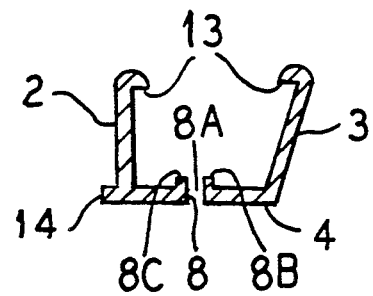
FIG. 3 is a sectional view of the bottom plate shown in FIG. 1, taken on the line III—III in FIG. 1.

FIG. 3 is a sectional view of the bottom plate 1, taken along the line III—III in FIG. 1. It can be seen from FIG. 3 that the outer defining wall 2 terminates substantially at right angles to the bottom surface 4, whereas the inner defining wall 3 slopes slightly away from the outer defining wall. The positioning of the separator 8 in the center of the bottom surface 4 is also illustrated in FIG. 3. Both the outer defining wall 2 and the inner defining wall 3 have at their upper ends mutually facing upper edges 13 which project slightly inwards from the wall and which function as attachment means for the cover member 15, as described below.

Located on the outside of the outer defining wall 2 are a pair of support shoulders 14 which form a support for a base former, which can be placed over the mold as described in more detail below.

As mentioned previously, FIG. 4 illustrates a cover member or mold insert 15. The cover member being configured to enable it to be placed in the bottom plate 1. Similar to the bottom plate 1, the cover member 15 is substantially U-shaped. The cover member 15 has a floor 16 which is bordered by an outer wall 17 and an inner wall 18. The bottom part 16 is smaller than the bottom surface 4 of the bottom plate 1 and both the outer wall and the inner wall are inclined at a greater angle relative to the outer and the inner defining walls of the bottom plate 1, so as to enable the cover member 15 to be snapped into the bottom plate 1. Alternatively or additionally, the cover member 15 could be ultrasonically welded into place.

As illustrated, the cover member 15 further includes perforations or holes 15A in the floor thereof. These perforations 15A are positioned to register with the channel 8A in the separator 8 when the cover member 15 is inserted in the bottom plate 1.

When impression material is placed in the cover member 15, a portion thereof will seep, ooze, or otherwise pass through the perforations 15A and the channel 8A. Thus, when the impression material hardens a portion thereof will harden on the underside of the cover member 15 and the bottom plate 1.

As a result, the impression material will be imparted with a good grip in the impression tray. This greatly assists in the removal of the impression from a patient's mouth.

Figure 5:
FIG. 5 is a side view of the cover member shown in FIG. 4.

FIG. 5 is a side view of the cover member 15. It can be seen from FIG. 5 that the height of the outer wall 17 preferably decreases or tapers toward the end of the cover member 15. In a corresponding manner, the height of the outer defining wall 2 decreases or tapers toward the ends 6 and 7 respectively.

Figure 4:
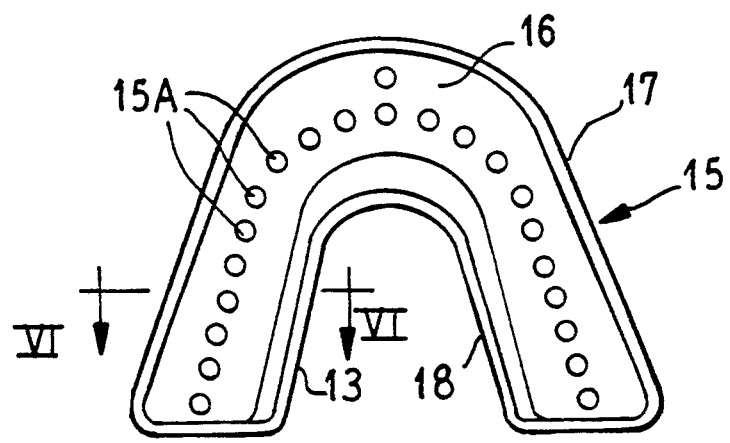
FIG. 4 is a plan view of a cover member or insert that can be placed on the bottom plate shown in FIG. 1, to form the complete mold in accordance with the inventions.
Figure 6:
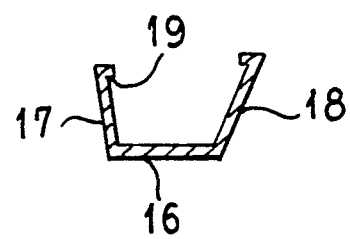
FIG. 6 is a sectional view of the cover member shown in FIG. 4, taken on the line VI—VI in FIG. 4.

FIG. 6 is a sectional view of the cover member 15, taken generally along the line VI—VI of FIG. 4, and illustrates the inclined outer wall 17 and the inclined inner wall 18. As can be seen from the Figure, both the outer wall 17 and the inner wall 18 are provided with inwardly projecting gripping edges 19 along their respective upper edges. It is conceivable to provide a gripping edge 19 solely on the inner wall or on the outer wall.

Figure 7:
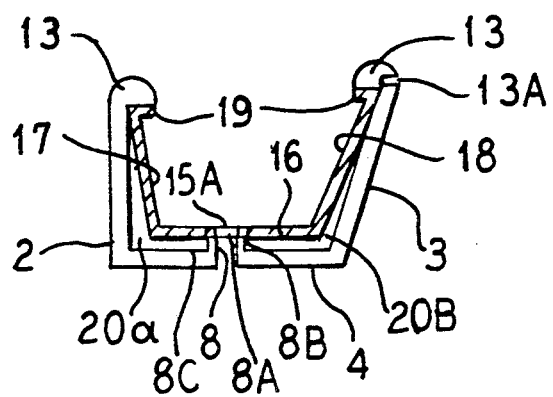
FIG. 7 is a sectional view of a bottom plate according to FIG. 1 with the cover member of FIG. 4 in position therein.

FIG. 7 is a sectional view of a bottom plate 1 with a cover member 15 inserted therein. It will be seen from the figure that the floor 16 of the cover member lies against the separator 8, and that the outer wall 17 of the cover member abuts the outer defining wall 2 of the bottom plate 1. The upper side of the gripping edge 19 on the outer wall 17 lies against the undersurface of the edge 13 of the outer defining wall. In a corresponding manner, the inner wall 18 abuts the inner defining wall 3, and the upper surface of the gripping edge 19 of said inner wall 18 lies against the undersurface of the edge 13 of the inner defining wall. As will be seen from the figure, there is formed in this way between the cover member 15 and the bottom plate 1 two channels 20a and 20b, which channels, as will be evident from FIG. 1, are in reality one single channel which leads from one connecting duct to the other.

Thus, when the cover member 15 is placed in position in the bottom plate 1, there is produced a mold for taking dental impressions which enables a coolant to be circulated through the mold, so as to enable the mold to be used with impression casting material which requires forced cooling with the aid of a coolant. At the same time the impression material can seep into the isolated channel 8A to provide a good grip thereof in the impression tray. The gripping edges 19 on the cover member 15 are intended to enable the cover member 15 to be gripped and removed from the bottom plate 1 when desired, for instance for cleaning the mold.

Figure 8:
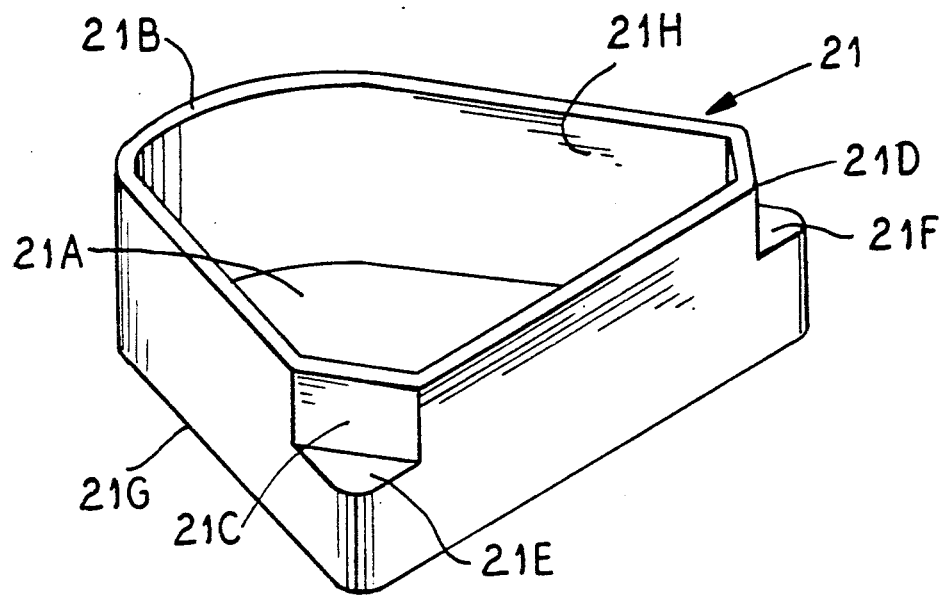
FIG. 8 is a perspective view of a base former that can be fitted over the mold so as to form a gypsum base.

FIG. 8 illustrates a base former 21 which is configured and dimensioned to be fitted over the bottom plate 1, optionally with the cover member or mold insert 15 inserted therein, so as to form an edge support for gypsum when gypsum is poured into the mold to form a gypsum base. When the base former 21 is fitted over the bottom plate 1, edge 21G of an upstanding wall 21B of the base former abuts the support shoulders 14 on the bottom plate 1 while an interior surface 21H of the wall 21B engages about the wall 2 of the bottom plate 1, thereby obtaining a positive and fixed support on the bottom plate 1. The bottom plate 1 is inserted through opening 21A.

The illustrated base former 21 is designed specifically for formation of a gypsum base for a lower jaw impression. The base former includes a plan view that substantially conforms in shape to the bottom plate 1.

As illustrated, the upstanding wall 21B includes two cut-off corners 21C and 21D at corners correlating to the backmost teeth in a jaw. The cut off corners 21C and 21D formed in the wall 21B eliminate any need to later cut off the corresponding corners in the resulting gypsum base for viewing of the gypsum teeth formation at the backside of the jaw. Thus, this base former eliminates steps that usually have to be undertaken, particularly when bases for both the upper and lower jaws are mated. Because of the cut-off corners 21C and 21D, two outer edges 21E and 21F, respectively, are formed over a position relating to the backmost teeth.

Figure 9:
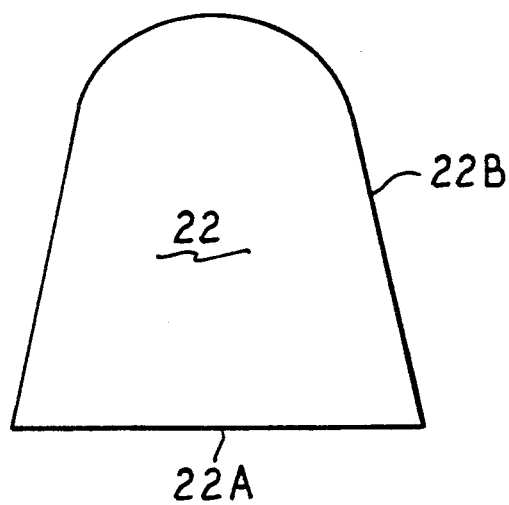
FIG. 9 illustrates palate plate which can be placed on the mold and in the base former so as to cover the palate-hole in the mold in the manufacture of the gypsum base.

FIG. 9 illustrates a palate plate 22 configured for positioning on the bottom plate 1 over the palate-hole 5 in when a gypsum base is to be cast, so as to prevent the gypsum from falling through the palate-hole. The palate plate 22 has a straight edge 22A which adjoins the straight edge of the upstanding wall 21B of base former 21 and a curved edge 22B that conforms to the curve defined by the inner wall 13. The palate plate 22 is appropriately pushed into a groove 13A provided in the edge 13A of the inner defining wall 3, from the rear end of the bottom plate 1 so as to be positively held by the bottom plate.

When the palate plate 22 is inserted in the groove 13 on the bottom plate 1, the mold can be used to take a full impression of the palate.

Figure 10:
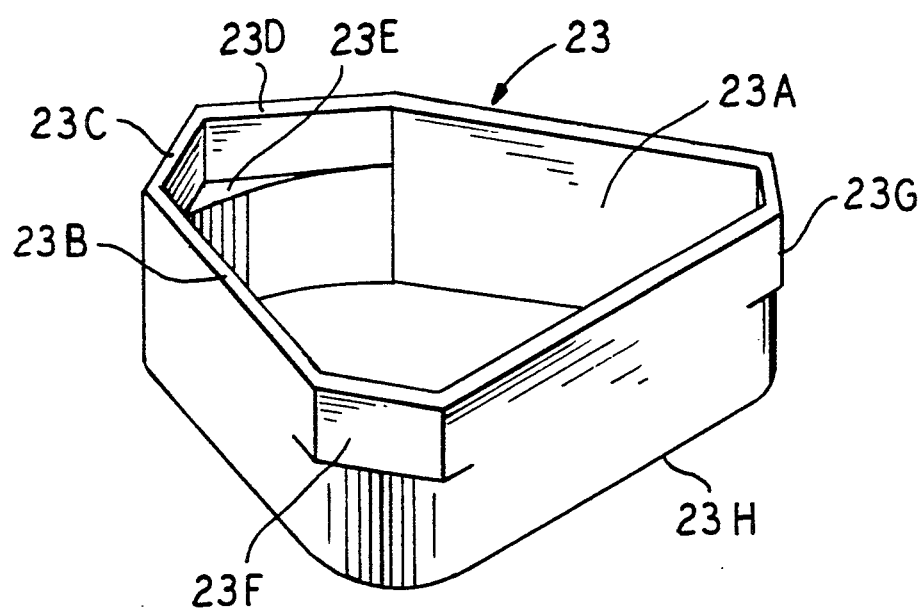
FIG. 10 is a perspective view of another base former that can be fitted over the mold so as to form a gypsum base.

FIG. 10 illustrates another base former 23 having an upstanding wall 23B configured and dimensioned to fit over the bottom plate 1, optionally with the cover member or mold insert 15 inserted therein, so as to form an edge support for gypsum when gypsum is poured into the mold to form a gypsum base. When the base former 23 is fitted over the bottom plate, edge 23H of the wall 23B abuts the support shoulders 14 on the bottom plate 1, thereby obtaining a positive and fixed support about the bottom plate 1. Interior wall 23A conforms about the bottom plate outer wall 2.

The base former 23 is designed for formation of a gypsum base for an upper jaw impression. The corners 23F and 23G comprise jutting boxes that form extending ledges in the resulting gypsum base. A triangular jutting wall portion is provided by walls 23C and 23D that protrude outward from a top portion of the wall 23B. As a result, a ledge 23E is formed within the former 23.

While a preferred embodiment has been shown, modifications and changes may become apparent to those skilled in the art which shall fall within the spirit and scope of the invention. It is intended that such modifications and changes be covered by the attached claims.

I claim:

1. A mold for taking dental impressions, comprising:
   a substantially U-shaped bottom plate having a bottom surface surrounded by inner and outer defining walls;
   a substantially U-shaped cover member or mold insert which can be inserted into the bottom plate and which is provided with a perforated floor and an inner wall and an outer wall which are upstanding from said floor and upper ends of which are intended to lie against upper ends of the defining walls, such that said floor of said cover member is spaced from the bottom surface of the bottom plate such as to form a coolant channel between the bottom plate and the cover member;
   an upstanding separator positioned on the bottom surface of the bottom plate against which said floor of the cover member is intended to lie so as to form two coolant channels on respective sides of the separator; and
   an upwardly opening channel formed in the separator that registers with said perforations in said cover member thereby isolating the perforations from the coolant channels.

2. The mold of claim 1, wherein the respective upper ends of the inner defining wall and the outer defining wall of the bottom plate are provided with mutually facing upper edges which project slightly inward from the walls.

3. The mold of claim 2, wherein the upper edge of at least one of said inner and said outer walls of the cover member is provided with an inwardly projecting gripping edge which is intended to abut the undersurface of the upper edge of the defining wall.

4. The mold of claim 1, wherein the mold is manufactured of a plastic material.

5. The mold of claim 4, wherein the plastic material comprises polysulfur.

6. The mold of claim 1, wherein the underside of the bottom plate is provided with a downwardly projecting camming surface which forms a grip active to facilitate removal of the mold from the mouth subsequent to having taken an impression.

* * * * *

UNITED STATES PATENT AND TRADEMARK OFFICE
CERTIFICATE OF CORRECTION

PATENT NO. : 5,127,829

DATED : 07/07/92

INVENTOR(S) : Martin Nordquist

It is certified that error appears in the above-identified patent and that said Letters Patent is hereby corrected as shown below:

Title page, 2nd column, 6 claims should read --9 claims--.

Column 6, add claims 7, 8 and 9.

7. The mold of claim 1, having connecting ducts at the front edge of the bottom plate in fluid communication with the contact chambers and a thumb-grip body which projects out from the front edge of the bottom plate which is configured to form an appropriate thumb-grip for removal of the mold subsequent to the making of a dental impression.

8. The mold of claim 1, wherein provided on the outside of the bottom edge of the bottom plate are support shoulders which support a base former which is used to form a gypsum base and which can be fitted over the mold.

UNITED STATES PATENT AND TRADEMARK OFFICE
CERTIFICATE OF CORRECTION

PATENT NO. : 5,127,829

DATED : 07/07/92

INVENTOR(S) : Martin Nordquist

It is certified that error appears in the above-identified patent and that said Letters Patent is hereby corrected as shown below:

9. The mold of claim 8 wherein the base former and the inner wall are configured to provide support for a palate plate which can be placed on the inner wall so as to form a foundation for gypsum used to form the gypsum base.

Signed and Sealed this

Sixteenth Day of February, 1993

Attest:

STEPHEN G. KUNIN

*Attesting Officer*  *Acting Commissioner of Patents and Trademarks*